United States Patent [19]

Kazuyuki et al.

[11] Patent Number: 4,987,262
[45] Date of Patent: Jan. 22, 1991

[54] CYCLOALKENE COMPOUNDS USEFUL IN RECORDING MATERIALS

[75] Inventors: Wakasugi Kazuyuki; Katsumasa Kikkawa; Masahiko Yamaguchi; Katsuichi Motohashi, all of Tokyo, Japan

[73] Assignee: Hodogaya Chemical Co., Ltd., Tokyo, Japan

[21] Appl. No.: 412,127

[22] Filed: Sep. 25, 1989

[30] Foreign Application Priority Data

Oct. 13, 1988 [JP] Japan .................. 63-255920

[51] Int. Cl.$^5$ ............................... C07C 211/55
[52] U.S. Cl. .................................... 564/443
[58] Field of Search ......................... 564/443

[56] References Cited

U.S. PATENT DOCUMENTS 4,912,259 3/1990 Kaneko et al. .......... 564/443 X

Primary Examiner—Richard L. Raymond
Attorney, Agent, or Firm—Sherman and Shalloway

[57] ABSTRACT

A novel cycloalkene compound represented by the following general formula [1]:

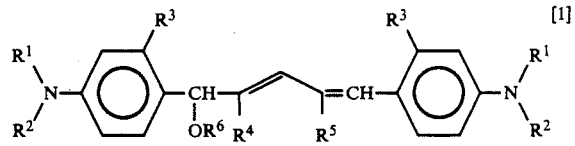

wherein each of $R^1$ and $R^2$ is a $C_1$–$C_4$ alkyl group, $R^3$ is a hydrogen atom, or a $C_1$–$C_4$ alkyl group, $R^4$, together with $R^5$, forms —$CH_2$—$CH_2$— or —$CH_2$—$CH_2$—$CH_2$—, and $R^6$ is a $C_1$–$C_4$ alkyl group.

3 Claims, No Drawings

CYCLOALKENE COMPOUNDS USEFUL IN RECORDING MATERIALS

BACKGROUND OF THE INVENTION

1 Field of the Invention

The present invention relates to a novel cycloalkene compound and a recording material which uses the compound as a color former.

2. Prior Art

Color formers, pale or colorless basic dyes, have been used in various recording materials such as pressure sensitive recording materials, heat sensitive recording materials, electrical heat sensitive recording materials, and photo sensitive recording materials. These recording materials are in great demand these days with the development of the information industry.

Typical color formers which have been used for recording materials such as pressure sensitive recording sheets, heat sensitive recording sheets and photo sensitive recording sheets, include phthalide compounds, fluoran compounds, and triphenyl methane compounds. For example, blue-coloring crystal violet lactone is a typical phthalide compound, black-coloring 2-(2-chloroanilino)-6-dibutylaminofluoran is a typical fluoran compound, and blue-coloring leucocrystal violet is a typical triphenyl methane compound.

Recently, computers have been employed widely for the rationalization of clerical works for office automation, or for the rationalization of various works for factory automation. For the input of information for such computers, various optical character readers or optical bar code readers have been developed in recent years.

With the progress of optical character readers or optical bar code readers where near infrared ray such as semi-conductor laser is used as a light source, recording materials suitable for these readers have been demanded Recording materials using previous color formers, however, were unsuitable for these new readers because the color formers had no light absorption in the near infrared region around 700-900 nm. Accordingly, recording images obtained from the previous recording materials were unsuitable for the recording images for the optical character readers or optical bar code readers which use near infrared ray as their light sources

SUMMARY OF THE INVENTION

A novel cycloalkene compound of the present invention represented by the following formula [1] is a novel color former which colors dense, bright green or bluish green, when contacted with a developing material.

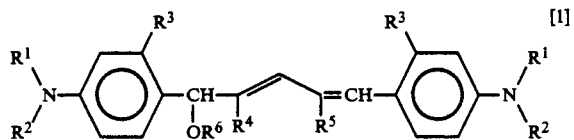

(wherein each of $R^1$ and $R^2$ is a $C_1$-$C_4$ alkyl group, $R^3$ is a hydrogen atom or a $C_1$-$C_4$ alkyl group, $R^4$ together with $R^5$, forms —$CH_2$—$CH_2$— or —$CH_2$—$CH_2$—$CH_2$—, and $R^6$ is a $C_1$-$C_4$ alkyl group)

DESCRIPTION OF THE PREFERRED EMBODIMENT

The developing material is an electronacceptor, such as an inorganic acid, an organic acid, a phenol compound, a derivative or metallic salt thereof, or an oxidizing agent. Typical developing materials include terra abla, 3,5-di-t-butyl salicylic acid, bis(3-chlorophenyl)thiourea, 4,4'-isopropylidene diphenol,4-nitro zinc benzoate, and 4- hydroxybenzyl benzoate. The recording material of the present invention is very useful for recently developed optical character or bar code readers where near infrared ray such as semi-conductor laser is used as their light sources because the recording image obtained from the recording material of the present invention such as pressure sensitive or heat sensitive recording sheet, absorbs light at the near infrared region of 700–900nm.

The present invention provides a novel cycloalkene compound and a recording material therefrom having excellent properties which previous color formers and recording materials did not have.

Typical examples of color developing materials used for pressure sensitive, heat sensitive, or photo sensitive recording materials are; bentonite, zeolite, terra abla, activated clay, silica gel, zinc oxide, zinc chloride, aluminium chloride, zinc bromide, organic acids such as maleic acid, succinic acid, malic acid and stearic acid, salicylic acid derivatives such as 3-t-butyl salicylic acid, 3,5-di-t-butyl zinc salicylate, and salicylic anilide, thiourea derivatives such bis(3-chlorophenyl)thiourea, phenol derivatives such as 4-t-butyl phenol,4-hydroxy diphenyl sulfone and 4-hydroxy benzophenone, naphthol derivatives, novolac phenol resin, benzoic acid derivatives such as 4-nitrobenzoic acid, 4-nitro zinc benzoate and 4-hydroxyethyl benzoate, naphthoic acid derivatives such a s1-hydroxy-2-naphthoic acid and 2-hydroxy-6-zinc naphthate, bisimidazole, hexaphenyl bisimidazole, and tetrabromo methane. Color formers of the present invention may be used alone or as a mixture of them or as a mixture with well known color formers such as crystal violet lacton, 2-(2-chloroanilino)-6-dibutylaminofluoran, 2-anilino-3-methyl-6-(N-ethyl-N-tetra hydrofurfurylamino) fluoran, 2-anilino-3-methyl-6-dibutylamino fluoran, 2-anilino-3-methyl-6-diethylamino fluoran, 2-anilino-3-methyl-6-(N-ethyl-N-isoamylamino) fluoran, 2-N,N-dibenzyl amino-6-diethylaminofluran, benzoylleucomethyleneblue, and leucocrystalviolet. Color development properties and storage stability of recording image may be improved by using mixed color formers. Typical solvents used in the pressure sensitive recording materials of the present invention are Hysol SAS-296(NIPPON PETROCHEMICALS CO., LTD), and KMC-113(KUREHA CHEMICAL INDUSTRY CO., LTD.). Various solvents such as monoisopropyl biphenyl, alkylbenzene, alkylbiphenyl, alkyl naphthalene, diaryl ethane, hydrogenized terphenyl, and chlorinated paraffin series solvents may be used alone or as a mixture thereof.

Various capsulation methods such as coacervation method, inter-facial polymerization method, and In-situ method can be used to prepare the pressure sensitive recording materials of the present invention Typical binders used to prepare heat sensitive recording materials include cellulose derivatives such as methyl cellulose and methoxy cellulose, starch and starch derivatives, polyvinyl alcohol, gum arabi, gelatin, casein, polyvinyl acetate, polyacrylic acid, polyvinyl pyrrolidone, poly-urethane, polyacrylamide, acrylamide/acrylic ester copolymer, and styrene/-maleic anhydride copolymer.

Various additives such as antioxidants, deterioration inhibitors and ultra-violet absorbers can be used in order to improve light resistance and storage stability of recording images. Examples of the above additives are esters of higher fatty acid, phthalic acid, or terephthalic acid, higher fatty acid amides, benzyl biphenyls, alkyl phenols, benzenesulfonamides, alkylbenzenesulfonamides and terphenyls.

The cycloalkene compound represented by the formula [I] can be synthesized by the following well known method as described in Japanese Patent Publication No.12802/1978, Japanese Unpatented Publication No.45785/1980 and Japanese Unpatented Publication No. 231766/1985.

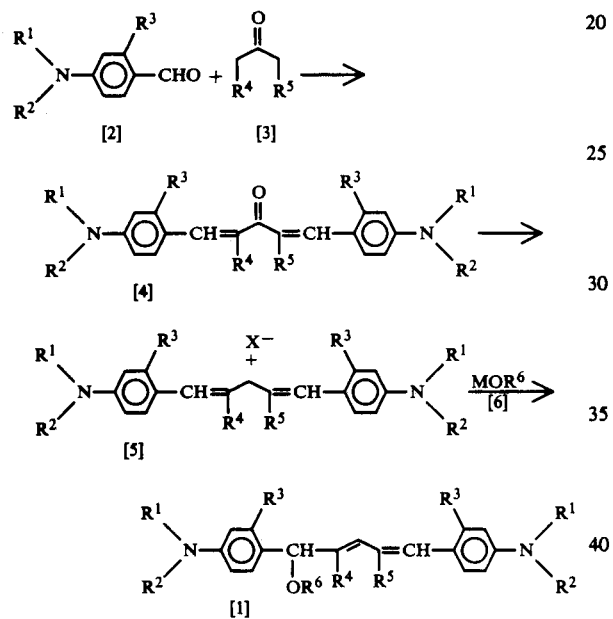

A cycloalkene derivative represented by the general formula [4] can be synthesized by dehydrocondensation of a benzaldehyde of the formula [2] and a cycloalkanone of the formula [3], in the presence of a basic catalyst such as sodium hydroxide, at 20°-70° C. for from several ten minutes to several hundred hours.

Further, a cycloalkenium salt derivative represented by the general formula [5], wherein X is a conjugate base, can be synthesized by reducing a cycloalkenone derivative of formula [4] in the presence of a catalyst such as palladium-carbon or in the presence of reducing agent such as sodium boron hydride, and then reacting the reduced product with an acid such as perchloric acid at 20°-100° C.

Further, a cycloalkene compound represented by the formula [1] can be synthesized by reacting the cycloalkenium salt derivative of the formula [5] with an alkali metal alcoholate of the formula [6], in an alcohol solvent such as methanol, at 20°-100° C.

In the formulas [2]-[6], $R^1$, $R^2$, $R^3$, $R^4$, $R^5$ and $R^6$ represent the same groups defined in the formula [1], and M represents an alkali metal.

The cycloalkene compounds thus synthesized are as follows.

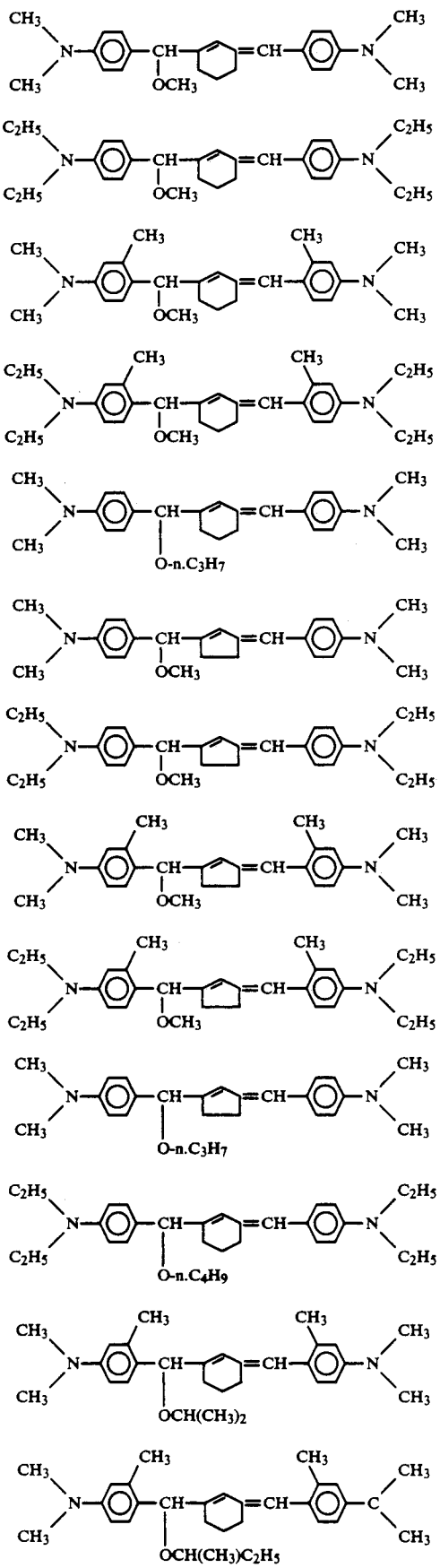

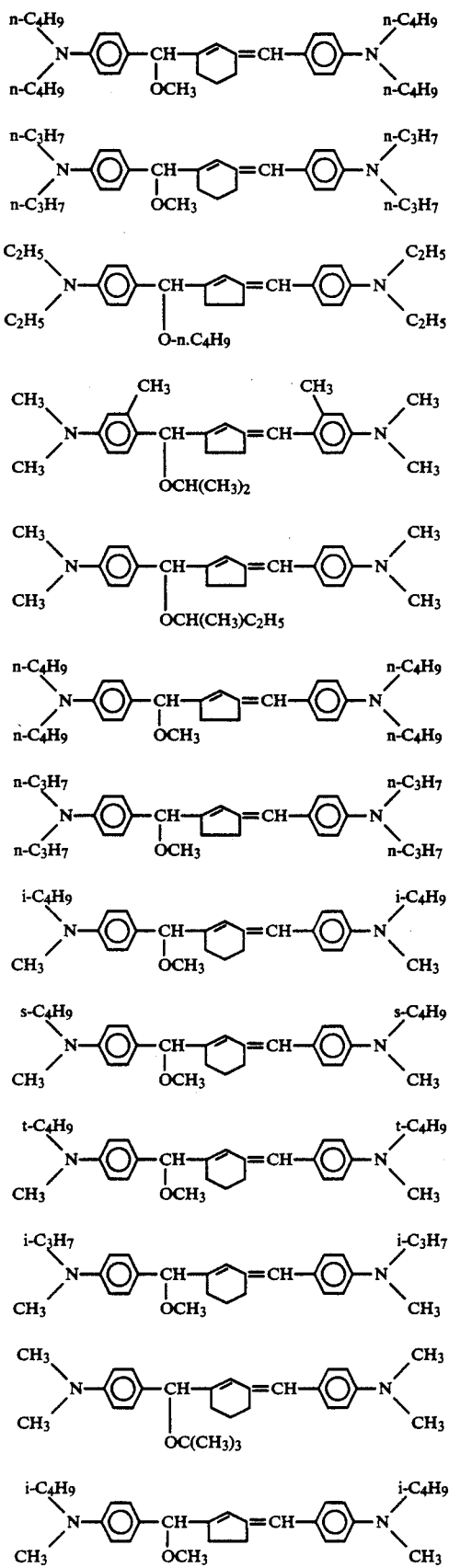

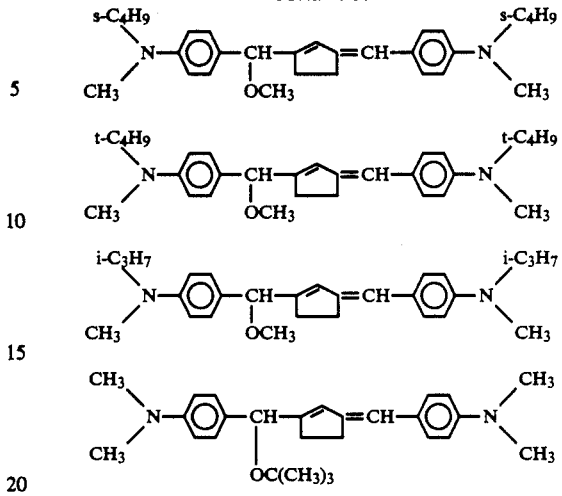

The present invention will be described in detail with reference to examples. In the following description, "parts" and "%" express "parts by weight" and "% by weight"

EXAMPLE 1

In order to synthesize 2,6-bis(4-N,N-dimethylaminobenzylidene) cyclohexanone, 20 parts of 4-N,N-dimethylamino benzaldehyde and 6.6 parts of cyclohexanone were dissolved in 40 ml of ethanol. 13.4 parts of a 10% sodium hydroxide aqueous solution was added to this, and the mixture thus obtained was reacted for 8 hours under stirring at 40°-50° C. Precipitated crystals were collected by filtration, washed with 30 ml of ethanol and then with 60 ml of water, and dried to yield 19 parts of orange yellow crystals. The product thus obtained was identified to be 2, 6-bis(4-N,N-dimethylaminobenzylidene) cyclohexanone, since it had a melting point from 240.0° to 243.0° C., and it had, by the $^{13}C$ NMR analysis, absorption peaks of one methylene carbon at 23.2 ppm and two methylene carbons at 28.7 ppm an absorption peak of methyl carbon attached to nitrogen at 40.2 ppm, an absorption peak of phenyl carbon attached to nitrogen at 150.3 ppm, and an absorption peak of carbonyl carbon at 190.1 ppm.

In order to synthesize 2,6-bis(4-N,N-dimethylamino benzylidene) cyclohexanium perchlorate, 10 parts of 2,6-bis (4-N,N-dimethylaminobenzylidene) cyclohexanone thus obtained, was dissolved in a solvent mixture of 100 parts of tetrahydro furfuryl alcohol and 150 parts of tetrahydrofuran, and then 1.1 parts of sodium boron hydride was added thereto. After the mixture was reacted for 8 hours at 30°-50° C., a mixture of 4.6 parts of 60% perchloric acid and 30 parts of glacial acetic acid was poured thereto at room temperature. Precipitated dark green crystals were collected by filtration, washed with water, and dried to yield 5 parts of 2,6-bis(4-N,N-dimethylamino benzylidene) cyclohexanium perchlorate.

In order to synthesize 1-[α-methoxy-(4-N,N-dimethylamino) benzyl]-3-(4-N,N dimethylaminobenzylidene) cyclohexene, 5 parts of 2,6-bis(4-N,N-dimethylamino benzylidene)cyclohexanium perchlorate thus obtained was dispersed in 50 parts of methanol, and then 2.4 parts of a 28% methanol solution of sodium methoxide was added thereto. The above mixture was reacted under reflux for one hour and then methanol was distilled out. The resulting product was extructed with 50 ml of toluene, washed with water, dried, and further toluene was distilled out to yield 2.9 parts of sticky yellow product. The product was identified to be 1-[α-methoxy-(4-N,N-dimethylamino)benzyl]-3-(4-N,N-dimethlyaminozenzylidene) cyclohexene. The $^{13}$C NMR analysis showed that the product had absorption peaks of methylene carbon at 23.0 ppm, 24.8ppm, and 27.2 ppm, an absorption peak of four methyl carbons attached to nitrogen at 40.6ppm, an absorption peak of a methine carbon attached to methoxy group at 87.0ppm, and absorption peaks of phenyl carbon attached to nitrogen at 149.0ppm and 150.1ppm.

The product was dissolved in a 95% acetic acid, and light absorption characteristics were measured. The product had the maximum absorption at 773nm.

EXAMPLE 2

In the same manner as described in Example 1, except that 5.6 parts of cyclopentanone was used instead of 6.6 parts of cyclohexanone, 20 parts of orange yellow crystal were obtained.

The product thus obtained had a melting point of from 28.10 to 290.0° C. By the $^{13}$C NMR analysis, the product was identified to be 2,5-bis(4-N,N-dimethylaminobenzylidene)cyclopentanone. It had an absorption peak of methylene carbon at 26.6ppm, an absorption peak of methyl carbon attached to nitrogen at 40.1ppm, an absorption peak of phenyl carbon attached to nitrogen at 150.7ppm, and an absorption peak of carbonyl carbon at 196.0ppm.

In the same manner as described in Example 1, except that 10.4 parts of 2,5-bis((4-N,N-dimethylaminobenzylidene) cyclopentanone was used instead of 10 parts of 2,6-bis(4-N,N-dimethylaminobenzylidene)cyclohexanone, 7.9 parts of dark green crystals of 2,5-bis(4-N,N-dimethylaminobenzylidene)cyclopentanium perchlorate were obtained.

In the same manner as described in Example 1(reacting, filtering, washing, and drying), except that 5 parts of 2,5-bis(4-N,N-dimethylaminobenzylidene)cyclopentanium perchlorate was used instead of parts of 2,6-bis(4-N,N-dimethylaminobenzylidene) cyclohexanium perchlorate, 3.6 parts of pale yellow crystals were produced.

The crystals thus obtained had a melting point of from 147.4 to 148.6° C. By the $^{13}$C NMR analysis, the product was identified to be 1-[α-methoxy-(4-N,N-dimethylamino)benzyl]-3-(4-N,N-dimetylaminobenzylidene)cyclopentene. It had absorption peaks of a methylene carbon at 29.1ppm and 32.2ppm, absorption peaks of methyl carbons attached to nitrogen at 40.5ppm and 40.6ppm, an absorption peak or methine carbon attached to a methoxy group at 82.8ppm, and absorption peaks of phenyl carbons attached to nitrogen at 150.1ppm and 150.2ppm.

The above cyclopentene was dissolved in a 95% acetic acid, and light absorption characteristics were measured. It showed the maximum absorption at 805nm.

EXAMPLE 3

In the same manner as described in Example 2, except that 21.9 parts of 2-methyl-4-N,N-dimethylaminobenzaldehyde was used instead of 20 parts of 4-N,N-dimethylaminobenzaldehyde, 15 parts of orange yellow crystals of 2,5-bis(2-methyl-4-N,N-dimethylamino benzylidene)cyclopentanone were produced. The product had a melting point of from 191.0 to 195.0° C. In the same manner as described in Example 2, except that 10 parts of 2,5-bis(2-methyl-4-N,N-dimethylaminobenzylidene) cyclopentanone was used instead of 10 parts of 2,5-bis(4-N,N-dimethylaminobenzylidene)cyclopentanone, 6 parts of dark green crystals of 2,5-bis(2-methyl-4-N,N-dimethylaminobenzylidene) cyclopentanium perchlorate were produced. In the same manner as described in Example 2, except that 5 parts of 2,5-bis(2-methyl-4-N,N-dimethylaminobenzylidene) cyclopentanium perchlorate was used instead of 5 parts of 2,5-bis(4-N,N-dimethylaminobenzylidene)cyclopentanium perchlorate, 3 parts of pale yellow crystals of 1-[α-methoxy-(2-methyl-4-N,N-dimethylamino)benzyl]-3-(2-methyl-4-N,N-dimethylaminobenzylidene) cyclopentene were produced. The product had a melting point of from 166° to 167° C.

The product was dissolved in a 95% acetic acid, and light absorption characteristics were measured. It showed the maximum absorption at 818nm.

EXAMPLE 4

In the same manner as described in Example 1, except that 21.9 parts of 2-methyl-4-N,N-dimethylaminobenzaldehyde was used instead of 20 parts of 4-N,N-dimethylaminobenzaldehyde, 14 parts of yellow crystals of 2,6-bis(2-methyl-4-N,N-dimethylaminobenzylidene)cyclohexanone were produced. The product thus produced had a melting point of from 211.0° to 214.0° C.

In the same manner as described in Example 1, except that 10.8 parts of 2,6-bis(2-methyl-4-N,N-dimethylaminobenzylidene) cyclohexanone was used instead of 10 parts of 2,6-bis(4-N,N-dimethylaminobenzylidene)cyclohexanone, 6,6 parts of dark green crystals of 2,6-bis(2-methyl-4-N,N-dimethylaminobenzylidene) cyclohexanium perchlorate were produced.

In the same manner as described in Example 1, except that 5 parts of 2,6-bis(2-methyl-4-N,N-dimethylaminobenzylidene) cyclohexanium perchlorate was used instead of 5 parts of 2,6-bis(4-N,N-dimethylaminobenzylidene)cyclohexanium perchlorate, 3.5 parts of pale yellow oil of 1-[-methoxy-(2-methyl-4-N,N-dimethylamino)benzyl]-3-(2-methyl-4-N,N-dimethylaminobenzylidene) cyclohexene was produced. The product thus prepared was dissolved in a 95% of acetic acid, and light absorption was measured. It showed the maximum absorption at 787nm.

EXAMPLE 5

The Preparation of Microcapsule Slurry

After 1.5 parts of 1-[-methoxy-(4-N,N-dimethylamino) benzyl]-3-(4-N,N-dimethylaminobenzylidene)cyclohexene of Example 1 was dissolved in 23.5 parts of KMC-113(KUREHA CHEMICAL INDUSTRY CO., LTD.), 12.6 parts of CORONATE L (NIPPON POLYURETHANE INDUSTRIES, LTD.) and 5 ml of ethyl acetate were added thereto under stirring Then a mixture of 3.5 parts of polyvinyl alcohol, 1.68 parts of gelatin, 2.86 parts of 1,4-di(2-hydroxy ethoxy) benzene and 54.96 parts of water, was added thereto After the whole mixture was emulsified with a homomixer under 6000rpm, 50 ml of water was added thereto and the emulsion thus prepared was heated at 60° C. to prepare a microcapsule slurry of 1-[α-methoxy-(4-N,N-dimethylamino)benzyl]-3-(4-N,N-di-methyl-amino benzylidene)cyclohexene dissolved oil.

The microcapsule slurry thus prepared was spread on a sheet of paper with a wire-bar-coater to get a uniform coating thickness, and the coated sheet was dried to prepare a CB paper.

The CB paper thus prepared was examined under 5 different environments; it was exposed to Fade-Ometer for 10 minutes; it was exposed to an environment of 90% relative humidity at 40° C., for 24 hours; it was exposed to a heat environment of 100° C., for 10 hours. Color densities of the tested papers were measured with a Macbeth reflection density meter RD-514, and compared with that of the unexposed CB paper. The results are tabulated below.

TABLE 1

| test conditions | V |
| --- | --- |
| unexposed | 0.05 |
| exposed to light for 10 min. | 0.06 |
| exposed to humidity for 24 hr. | 0.05 |
| exposed to heat for 10 hr. | 0.05 |

(V means visual filter)

As clearly understood from table 1, color density of CB paper scarcely changed after the exposure to light, humidity, or heat. It means that the CB paper of the present invention has an excellent property showing no fogging.

Further, fresh CB papers were contacted with commercially available typical color developing sheets, and a pressure of 500 kg/cm² by oil press was applied to each of the 28 mm sheets, whereby recording images developing greenish blue or bluish green were obtained. The color developing sheets used here were clay, resin and metallic salt of salicylic acid derivative series color developing sheets.

Color densities of the recording images thus obtained were measured by a spectrophotometer U-3410 (HITACHI LTD.). The reflectivity of the recording image obtained by a clay series color developing sheet was 6.6%, when measured at the wave length of 788 nm in the near infrared region.

After the recording images thus obtained were exposed to Fade-Ometer for one hour, reflectivities of the images were measured to determine their light discoloration resistances. The reflectivitirs of the unexposed recording image and the exposed recording image were, when developed by, for example, clay series developing sheet, 6.6% and 11.9%, respectively.

Further, after fresh CB papers were exposed to Fade-Ometer for 10 minutes, they were contacted with commercially available typical pressure sensitive color developing sheets-clay, resin, and metallic salt of salicylic acid derivative series color developing sheets, respectively, and then a pressure of 500 kg/cm² by oil press was applied to the 28 mm, φof the pressure sensitive papers thus prepared to develop color. Reflectivities of the recording images thus obtained were measured to determine color-developing properties after light exposure. The reflectivities of the images obtained from fresh, unexposed CB paper and from the exposed CB paper, developed by for example, clay series developing sheets, were 6.6% and 9.8%, respectively.

In the same manner as described above, light discoloration resistances of the recording images and color-developing properties after light exposure of the recording sheets, developed by resin and metallic salt of salicylic acid derivative series color developing sheets, were measured. The results are tabulated in Table 2.

TABLE 2

| measured at the wave length of 788 nm | reflectivity (%) | | |
| --- | --- | --- | --- |
| | clay | resin | metallic salt of salicylic acid |
| developed color density | 6.6 | 4.9 | 6.3 |
| light discoloration resistance 1 hr. | 11.9 | 28.1 | 40.4 |
| color-developing properties after exposure 10 min. | 9.8 | 6.4 | 8.6 |

As clearly understood from table 2, both types of commercially available color developing sheets could develop recording images having high color densities, low discoloration after light exposure, and high color-developing properties after light exposure.

As clearly understood from Tables 1 and 2, the pressure sensitive recording sheets of the present invention where the compound synthesized in Example 1 was used, could give the recording images having very high color densities and very low light discoloration The CB papers of the present invention had very high color-developing properties after exposure to light, and very low fogging The pressure sensitive recording sheets of the present invention had excellent color developing properties and storage stabilities.

EXAMPLE 6

Preparation of "Slurry A"

A colorless slurry was prepared by dispersing and mixing 2 parts of 1-[α-methoxy-(4-N,N-dimethylamino) benzyl]-3-(4-N,N-dimethylaminobenzylidene)cyclopentene of Example 2 and 20 parts of a 10% polyvinyl alcohol aqueous solution with a ball mill at room temperature for 24 hours. The particle size of the solid substance in the slurry was about 3 micron.

Preparation of "Slurry B"

Slurry B was prepared by mixing 7.5 parts of bisphenol A, 40 parts of a 10% polyvinyl alcohol aqueous solution and 10 parts of deionized water at room temperature for 24 hours. The particle size of the solid substance in the slurry B was about 5 micron.

A mixed slurry was prepared by mixing the slurries A and B, and then stirring the mixture at room temperature for one hour. The mixed slurry thus prepared was coated on a sheet of paper (50g/m²) with a bar coater to get a uniform thickness, and the coated paper was air dried at room temperature to prepare a heat sensitive recording sheet having colorless, heat sensitive layer thereon.

The heat sensitive recording sheet thus prepared was color developed by a heat-gradient tester. A yellowish green recording image was obtained. The measurement of the reflective absorption properties showed that the recording image had a strong electro magnetic wave absorption in near infrared region.

As described above, the present invention provides a novel cycloalkene compound and a recording material which uses said compound as a color former. The compound has a strong absorption in the near infrared region when developed, an excellent solubility to capsule oils when used in a pressure sensitive recording sheet, excellent developing and storage properies, and an excellent sensitivity when used in a heat sensitive recording sheet. The present invention meets the demand of new markets and develops a lot of new use of recording materials.

We claim:

1. A cycloalkene compound represented by the following general formula [1]:

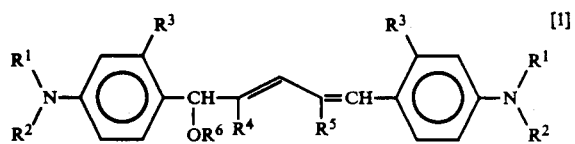

wherein each of $R^1$ and $R^2$ is a $C_1$-$C_4$ alkyl group, $R^3$ is a hydrogen atom, or a $C_1$-$C_4$ alkyl group, $R^4$ together with $R^5$, forms —$CH_2$—$CH_2$— or —$CH_2$—$CH_2$—$CH_2$—, and $R^6$ is a $C_1$-$C_4$ alkyl group.

2. The cycloalkene compound according to claim 1, wherein each of $R^1$, $R^2$ and $R^6$ is methyl group, $R^3$ is a hydrogen atom and $R^4$ together with $R^5$, forms —$CH_2$—$CH_2$—.

3. The cycloalkene compound according to claim 1, wherein each of $R^1$, $R^2$, $R^3$ and $R^6$ is methyl group, and $R^4$ together with $R^5$, forms —$CH_2$—$CH_2$—$CH_2$—.

* * * * *